US005578474A

United States Patent [19]
Focht et al.

[11] Patent Number: 5,578,474
[45] Date of Patent: Nov. 26, 1996

[54] PROCESS FOR CULTURING RECOMBINANT MICROORGANISMS

[75] Inventors: Dennis D. Focht, Riverside, Calif.; Lothar P. Kröckel, Thurnau, Germany

[73] Assignee: The Regents of the University of California, Oakland, Calif.

[21] Appl. No.: 259,283

[22] Filed: Jun. 13, 1994

Related U.S. Application Data

[63] Continuation of Ser. No. 927,793, Aug. 10, 1992, abandoned, which is a continuation of Ser. No. 581,247, Sep. 7, 1990, abandoned, which is a continuation-in-part of Ser. No. 74,847, Jul. 17, 1987, abandoned.

[51] Int. Cl.$^6$ .................. C12N 1/21; C12N 1/00; C12N 15/00
[52] U.S. Cl. .................. 435/172.3; 435/172.1; 435/252.3; 435/252.34; 435/823; 435/829; 435/830; 435/874
[58] Field of Search .................. 435/252.34, 252.3, 435/252.4, 253.6, 874, 813, 819, 172.1, 172.3, 823, 829, 874, 830

[56] References Cited

U.S. PATENT DOCUMENTS 4,535,061  8/1985  Chakrabarty et al. .................. 435/252.4

OTHER PUBLICATIONS

Munnecke et al. Applied Microbiology vol. 28 pp. 212–217 (1974).
Davis et al. Microbiology, 2nd Edition Harper & Row Publishers (1973).
Kilbane et al. Appl. Environ. Microbiol. vol. 44 pp. 72–78 (1982).
Pirt, SJ. J. Appl. Chem. Biotechnol. vol. 22 pp. 55–64 (1972).
Beringer et al., pp. 63–70 in *Current Perspectives in Microbial Ecology*. (ed. Klug & Reddy 1984).
DeBont et al., Appl. Environ Microbiol. 52(4):677–680 (Oct. 1986).
Hayes, pp. 268–299 in *Papers on Bacterial Genetics* (ed. Adelberg 1960).
Hopwood, pp. 1–9 in *Genetics of Industrial Microorganisms* (ed. Sebek & Laskin 1979).
Kellogg et al., Science 214: 1133–1135 (Dec. 4, 1981).
Levin et al., Plasmid 2 247–260 (1979).
Levin et al., Genet. Res. Camb. 35: 241–259 (1980).
Levin et al., Genetics 94: 425–443 (Feb. 1980).
Reineke et al., Appl. Environ. Microbiol. 47(2):395–402 (Feb. 1984).
Schraa et al., Appl. Environ. Microbiol. 52(6): 1374–1381 (Dec. 1986).
Slater, pp. 89–98 in *Engineered Organisms in the Environment: The Scientific Issues* (ed. Halvorson et al. 1985) [*Slater I*].
Slater, pp. 87–93 in *Current Perspectives in Microbial Ecology* (ed. Klug & Reddy 1984) [Slater II].
Wollman et al., pp. 300–334 in *Papers on Bacterial Gentics* (ed. Adelberg 1960).

*Primary Examiner*—George C. Elliott
*Assistant Examiner*—Thomas G. Larson
*Attorney, Agent, or Firm*—Robbins, Berliner & Carson

[57] ABSTRACT

A recombinant microorganism strain having a desired metabolic property is produced by a process which utilizes a multiple chemostat system.

7 Claims, 4 Drawing Sheets

PROCESS FOR CULTURING RECOMBINANT MICROORGANISMS

This is a continuation of Ser. No. 07/927,793 filed Aug. 10, 1992, now abandoned, which in turn is a continuation of Ser. No. 07/581,247 filed Sep. 7, 1990, now abandoned, which in turn a continuation-in-part of Ser. No. 07/074,847 filed Jul. 17, 1987, now abandoned.

BACKGROUND OF THE INVENTION

1. Field of the Invention

This invention relates to a process for constructing a recombinant strain of microorganisms which has desirable metabolic characteristics. In one of its more particular aspects, this invention relates to a multiple continuous culture method for producing recombinant bacteria. In another of its more particular aspects, this invention relates to the construction of a strain of microorganisms which is useful in the disposal of toxic wastes such as halogenated organic compounds.

Halogenated organic compounds, such as chlorobenzenes, are used in a wide variety of synthetic and utilitarian applications in industry, agriculture and health care. For example, halogenated organic compounds are used in dielectric fluids, flame retardants, refrigerants, heat transfer fluids, protective coatings, pesticides and other chemical products. Disposal of these materials after use in halogenated by-products of their production poses a serious problem because of the toxicity of these halogenated organic compounds. The disposal of toxic waste has, in recent years, achieved such huge proportions that storage of toxic chemicals in landfills and other areas designated for storage thereof no longer satisfies the ever growing need for safe and efficient disposal of these materials.

2. Prior Art

Many different methods have been proposed for rendering toxic waste innocuous. Among these are incineration, chemical transformation and microbiological degradation. Because microbiological degradation of toxic waste does not involve the use of chemical reagents which might themselves be toxic and does not result in the production of large amounts of noxious fumes, such as produced in the incineration of toxic waste, it has become a preferred method of disposing of toxic waste.

Most microbiological degradations of toxic materials are based upon discovering a particular microorganism which will metabolize a toxic material, converting it to innocuous metabolic products, usually, in the case of organic compounds, carbon dioxide, water and salts. Finding microorganisms which can efficiently and safely convert toxic wastes into innocuous metabolic products is a highly complex procedure involving many arduous steps and requiring a significant expenditure of time.

One such procedure is taught in U.S. Pat. No. 4,493,895, wherein is described a process for microbial degradation of obnoxious organic wastes into innocuous materials. This process comprises the steps of (1) collecting a sample of material from the site contaminated with obnoxious chemicals; (2) enriching the microorganisms found living in the sample; (3) separating the strains of microorganisms capable of having different metabolisms for the various chemicals in the sample from the site, from each other; (4) purifying the strains which are capable of biodegrading the chemicals to be disposed of; (5) applying the strain to the locales of the contaminants to be disposed of; and (6) monitoring of removal of the contaminants at the locales of the contamination. It can be seen that this is indeed an involved procedure requiring large amounts of time and effort.

Another approach taught in U.S. Pat. No. 5,511,657, involves a process of treating chemical waste landfill leachates with activated sludge containing bacteria capable of metabolizing obnoxious organics present in the leachate.

U.S. Pat. No. 4,664,805, assigned to the same assignee as the present invention, describes a process in which environments contaminated with toxic halogenated organic compounds are decontaminated at an accelerated rate by the addition of (1) microorganisms which are non-indigenous to the environment in which it metabolizes a contaminant at a greater rate than microorganisms indigenous to the environment; and (2) a non-toxic analog of the halogenated organic compound.

The foregoing references describe processes in which reliance is placed upon naturally occurring microorganisms. Another approach involves the production of microorganisms having the same desired metabolic properties by genetic engineering or various related procedures. An example of such method is shown in U.S. Pat. No. 4,535,061 wherein plasmid-assisted molecular breeding procedures for generating pure and mixed cultures of microorganisms capable of dissimilating environmentally persistent chemical compounds are described.

Microorganisms which utilize chlorinated aromatic hydrocarbons as sole carbon sources cannot normally be isolated by conventional enrichment culture techniques. Nevertheless, many aromatic hydrocarbon-utilizing bacteria can co-metabolize these compounds. The dead end products formed from co-metabolism in pure culture may be further metabolized to $CO_2$, HCl and $H_2O$ by other microbial species as noted in the mineralization of PCB's in soil as described in W. Brunner, F. H. Sutherland and D. D. Focht, Enhanced Biodegradation of Polychlorinated Biphenyls In Soil by Analog Enrichment and Bacterial Inoculation, J. Environ. Qual. 14:324–328, 1985. Similar processes are described in D. D. Focht and W. Brunner, Kinetics of Biphenyl and Poly-chlorinated Biphenyl Metabolism in Soil, Appl. Environ. Microbiol. 50:1058–1063, 1985.

The mobilization of the requisite gene pool into a single species would be a desirable goal for complete mineralization of a target compound. Recombinants are obtained by genetic engineering techniques or by natural genetic exchange between bacteria. The former method is very tedious and time consuming, and is frequently limited by the lack of commercially available degradation products for isolation of clones specific for given catabolic functions. Natural genetic exchange, on the other hand, involves very little labor, but requires considerable patience and luck since the requisite organisms may either not exist or be present in such low numbers that the frequency of the desired genetic exchange event may be too low to be manifested over the observation period.

For example, enrichment cultures of Alcaligenes sp. that grew on 1,4-dichlorobenzene (1,4-DCB) required at least ten months for isolation as described in G. Schraa, M. L. Boone, M. S. M. Jetten, A. R. van Neervaen, P. J. Colberg and A. J. B. Zehnder, Degradation of 1,4-dichlorobenzene by Alcaligenes sp. strain A175, Appl. Environ., Microbiol. 52:1374–1381, 1986.

Similarly, cultures growing on 1,3-dichlorobenzene (1,3-DCB) required at least six months for isolation as described in J. A. M. DeBont, M. J. A. W. Vorage, S. Hartmans and W. J. J. van den Tweel, Microbial Degradation of 13 Dichlorobenzene, Appl. Environ. Microbiol. 52:677–680, 1986.

Nine months of continuous selection pressure in a chemostat was required before growth on chlorobenzene (CB) with strain WR 1306, which was originally isolated from enrichment with benzene as described in W. Reineke and H.-J. Knackmuss, Microbial Metabolism of Haloaromatics: Isolation and Properties of a Chlorobenze-Degrading Bacterium, Appl. Environ. Microbiol. 47:395–402, 1984.

If two or more organisms together, but not separately, possess the catabolic enzymes for complete mineralization of a substrate, then it should theoretically be possible to construct a recombinant strain that would grow with that substrate as its sole carbon source if selection pressures can be optimized separately for the recombinant and the parental strains.

It is accordingly an object of the present invention to provide a process for the construction of a recombinant strain of microorganism which possesses the combined catabolic enzymes present in the parent bacteria. Another object of this invention is to provide a process for constructing recombinants which proceeds at a faster rate than previously available processes. Other objects and advantages of the present invention will become apparent in the course of the following detailed description.

SUMMARY OF THE INVENTION

The present invention provides a commercially useful process for constructing recombinant strains of microorganisms having desirable metabolic characteristics. The process utilizes parent microorganisms having metabolic properties closely related to the metabolic properties desired in the recombinant in a process in which natural genetic exchange and imposed selective pressures combine to achieve the creation of a desired recombinant strain. The process utilizes a multiple continuous culture method.

In particular, the present invention provides a means for cumulating a rare event, namely genetic exchange between two or more species of microorganisms, over time. The process of the present invention opens the door to the provision of microorganisms having desired metabolic properties without the necessity for the complicated procedures and involved techniques of genetic engineering. For example, a microorganism having the metabolic capabilities of degrading a recalcitrant or persistent organic chemical, such as a halogenated hydrocarbon, can be produced by genetic interchange between two species of microorganisms each having metabolic properties closely allied to the metabolic properties desired of the recombinant strain. For example, a strain of microorganisms capable of degrading chlorobenzene (CB) can be produced by genetic interchange between a microorganism strain having the capability of degrading 3-chlorobenzoate (3CB) and a microorganism strain capable of degrading toluene.

The process consists of culturing each parent strain of microorganism separately in a chemostat applying the resulting combined culture to a column upon which the microorganism combined culture can be adsorbed, and introducing the effluent from the column into a third chemostat containing the organic compound which the recombinant is designed to metabolize as the sole source of carbon for the growth of the recombinant. The recombinant is then isolated from the third chemostat by conventional procedures.

DESCRIPTION OF THE PREFERRED EMBODIMENTS

In a preferred embodiment, the present invention makes use of a multiple chemostat system employing separate optimal growth of two parental strains with steady state constant selective pressure to ensure the reduction of the rare event of genetic interchange to cumulative common probability of occurrence.

The invention will be illustrated with respect to a process for constructing a bacterium capable of metabolizing chlorobenzene (CB) utilizing two bacteria, neither of which is capable of growing on chlorobenzene but which together have all the necessary catabolic enzymes for complete metabolism of chlorobenzene.

Figure 1:
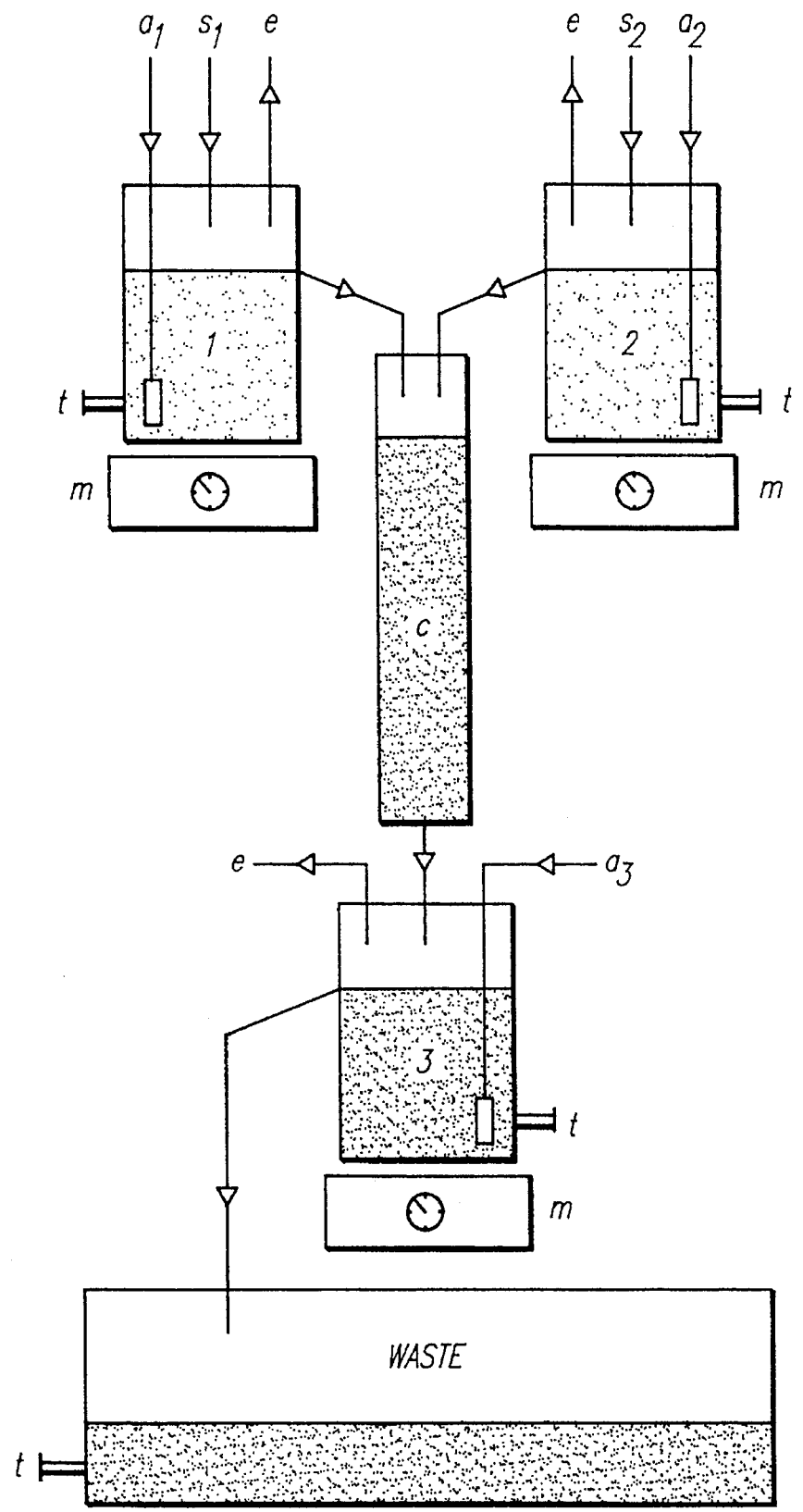
FIG. 1 drawing is a schematic diagram of a system for carrying out the process of the present invention.

Referring to FIG. 1 numerals 1, 2 and 3 designate three chemostat stages, c is a ceramic bead column, and the vessel labeled "waste" is the depository for overflow from chemostat stage 3. Sampling points t in each of the chemostats permit samples to be removed for analysis and magnetic stirrers m insure that adequate mixing takes place in each chemostat stage. Inputs to chemostat stage 1 are air, designated $a_1$, and a mineral salts medium with 2 mM benzoate, designated $s_1$. Gaseous exhaust from each chemostat stage is designated e. Inputs to chemostat stage 2 are toluene saturated air, designated $a_2$ and a mineral salts medium designated $s_2$. Overflows from chemostat stages 1 and 2 are shown being applied to ceramic bead column c. Effluent from column c constitutes one of the inputs to chemostat stage 3, the other input being chlorobenzene saturated air, designated $a_3$. Overflow from chemostat stage 3 is shown being removed to the waste vessel.

Many different environments contaminated with toxic halogenated organic compounds can be decontaminated by means of the process of the present invention. In particular, soils contaminated with such halogen-containing compounds can be rid of the contaminants at a rate which is within practical limits. Aqueous and gaseous environments can be also suitably treated according to the process of the present invention.

A wide variety of toxic halogen containing contaminants find their way into natural environments such as soil, ground water and the atmosphere. Agricultural contaminants which can be degraded according to the process of the present invention include, for example, Heptachlor, Aldrin, Dieldrin, 4,4'-DDE, 4,4'-DDT, endrin, 4,4'-DDD, Heptachlor Epoxide, Chlordane, Endrin Aldehyde, hexachlorobenzene, and a wide variety of polychlorobiphenyls (PCB's) including Aroclor 1016, 1231, 1232, 1242, 1248, 1254, and 1260. Other chemical contaminants include bis(2-chloroethyl)ether, 1,3-dichlorobenzene, 1,4-dichlorobenzene, 1,2-dichlorobenzene, bis(2-chloroisopropyl)ether, hexachloroethane, bis(2-chloroethoxy)methane, 1,2,4-trichlorobenzene, hexachlorobutadiene, hexachlorocyclopentadiene, 2-chloronaphthalene, 4-chlorophenyl phenyl ether, 4-bromophenyl phenyl ether, 2-chlorophenol, 2,4-dichlorophenol, 4-chloro- 3-methylphenol, 2,4,6-trichlorophenol, pentachlorophenol, methylene chloride, trichlorofluoromethane, 1,1-dichloroethylene, 1,1-dichloroethane, 1,2-dichloroethylene, chloroform, 1,2-dichloroethane, 1,1,2-trichloroethane, 1,1,1-trichloroethane, bromodichloromethane, 1,2-dichloropropane, trichloroethylene, 1,3-dichloropropane, bromoform, 1,1,2,2-tetrachloroethane, 1,1,2,2-tetrachloroethylene, chlorobenzene, methyl bromide, carbon tetrachloride, 2-chloroethyl vinyl ether, bis(chlorethyl)ether and dichlorodifluoromethane. Other agricultural contaminants including various other pesticides and herbicides and other halogen-containing organics from various sources including industrial wastes can also be similarly treated.

In addition, microorganisms which convert various substrates to antibiotics, hormones, vitamins and other useful biological chemicals can be constructed in accordance with the process of the present invention.

The process of the present invention will be better understood by reference to the following examples.

EXAMPLE 1

Construction of Recombinant Capable of Growing on Cholorbenzene.

*Pseudomonas alcaligenes* C—O and *Pseudomonas putida* R5-3 were isolated by direct enrichment in stationary culture from activated sewage sludge with 3-chlorobenzoate and toluene, respectively, as the single carbon energy sources as described in D. Shelton and D. D. Focht, Kinetics of 3-Chlorobenzoate Metabolism in Culture and in Soil, Agron. Abstr., p.117, 1985. Liquid cultures were incubated at 27° C. on a rotary shaker at 120 rpm. Stock cultures were maintained on mineral medium with the selective carbon source, subcultured monthly, and stored at 4° C.
Media.

A mineral salts medium was used consisting of 20 mM phosphate buffer ($KH_2PO_4$, $Na_2HPO_4$; pH 7.2), 0.5 g/l $(NH_4)_2SO_4$, 0.2 g/l $MgSO_4$, $7H_2O$ in deionized water supplemented with 10 ml/l of chloride-free trace element stock solution containing the following (in mg/l): $Ca(NO_3)_2.4H_2O$ (600); $FeSO_4. 7H_2O$ (200); $MnSO_4.4H_2O$ (20); $CuSO_4.5H_2O$ (40); $ZnSO_4.7H_2O$ (20); $H_3BO_3$ (3); and $NaMoO_4.2H_2O$ (4). The stock solution was acidified with 1 ml/l of concentrated sulfuric acid. Substrates were added at a final concentration of 0.1% or supplied as saturated atmospheres in dessicators, or, in the case of benzene, 20–40% of the atmosphere was exchanged against benzene-saturated air. LB (T. Maniatis, E. F. Fritsch and J. Sambrook, Molecular Cloning—a Laboratory Manual, Cold Spring Harbor Laboratory Press, Cold Spring Harbor, N.Y., 1982) and King's B (E. O. King, M. K. Ward and D. E. Raney, Two Single Media For the Demonstration of Pyocyanin and Fluorescein, J. Lab. Clin. Med. 44: 3d-307, 1954) medium were used for strain maintenance and verification. All substrates, except toluene, chlorobenzene, benzene, and xylene, were added prior to autoclaving (121° C). Solid media contained 1.5–2.0% of Bactoagar (Difco, Mich.). When 1,4-dichlorobenzene was used as a carbon source mineral agar plates were sealed with parafilm and incubated upside down with a few crystals of the substrate in the lower lid of the Petri dish. Bromothymol blue (40 mg/l) was added to detect acidification. Chloride release on solid medium was detected by flushing plates with a 0.1M silver nitrate solution in 5M phosphoric acid.

Chloride was determined in culture supernatants by adding 0.5ml of the above silver nitrate solution to 5 ml of sample and reading the absorbance at 525 nm (Beckman DB-G spectrophotometer). Optical densities (O.D.) of cell suspensions were measured at 546 mm.

Continuous culture of *P. alcaligenes* C—O and *P. putida* R5-3 were grown separately at three different dilution rates (0.005, 0.007, 0.011 $hr^{-1}$) in three parallel setups according to the scheme in the drawing. The chemostats contained 400 ml of medium. Toluene and chlorobenzene were supplied in the vapor form with the incoming air at a flow rate of 200 and 670 ml/min, respectively. The incoming air was filtered through 5-cm cotton filters. The benzoate-chemostats contained 2 mM benzoate and were aerated at a rate of 333 ml air $min^{-1}$. The whole system was autoclaved before use and run at 22° C. The chemostats were inoculated from late exponential cultures (1/100), and the bacteria were grown to an O.D. of 0.5–0.8 before liquid flow was started to maintain a steady-state cell density. The overflow from both cultures was combined on a column filled with ceramic beads (4 mm diameter) to increase the cell density and cell to cell contact while decreasing the rate of washout. The column outflow dropped into a third chemostat where chlorobenzene was supplied as the only source of energy and carbon. Samples for chloride analysis were taken daily from the chlorobenzene chemostats. Cell-free extracts were prepared from washed cell suspensions at 0° C. in the presence of 10% acetone by applying six five-second bursts with a Sonfier Cell Disruptor Model W185 (Heat Systems Ultrasonics, Inc., Plainview, N.Y.) at maximum output. The extracts were clarified at 40,000 rpm at 4° C. in a Beckman TL-100 ultra-centrifuge. Meta-pyrocatechase (MP) (EC 1.13.11.2) and ortho-pyrocatechase (OP) (EC 1.13.11.1) were determined as described previously (Dorn and Knackmuss, 1978; Reineke and Knackmuss, 1984). Fresh cell-free extracts were incubated at 55° C. to inactivate OP or treated with $H_2O_2$ to inactivate MP. Molar extinction coefficients of the ring-fission products were estimated as described previously (Dorn and Knackmuss, 1978). Specific activities were expressed as milliunits (1 mU=1 nanomole of substrate utilized per minute) per milligram of protein at 30° C.
Plasmids.

Plasmid DNA was isolated using the alkali lysis procedure and purified by ultracentrifugation on a cesium gradient (Maniatis et al., 1982). Agarose gels (0.7%) were run for 1 hour at 10 V $cm^{-1}$. Restriction enzymes were used following the recommendations of the supplier.

Curing experiments were performed by; a) subcultivating strains on benzoate and LB agar plates 5–10 times; and b) subcultivating the strains 3 times in LB broth supplemented with ethidium bromide (100–800 mg /l) overnight followed by a 1-hour incubation at 42° C. Colonies from dilution series on LB agar plates then were tested for growth on selective media.
Conugation Experiments.

Conjugation experiments were carried out on LB agar plates according to Maniatis et al. (1982). After growth microorganisms were resuspended, plated on mineral medium and incubated in a chlorobenzene saturated atmosphere.

After running the chemostats in accordance with the scheme shown in the drawing for 1 week, all three chemostats with *P. putida* R5-3 were yellow-colored as a result of the metaring fission product of toluene metabolism, while the three chemostats containing *P. alcaligenes* C—O were white. There were notable differences among the three bottom chemostats that received the effluent from the mixed reactor column. The chemostats at the higher dilution rates (0.007 and 0.011 hr$^{-1}$) was brownish-black in color and did not contain inorganic chloride. (The brownish-black color is due to the formation of quinones and chemical polymerization of chlorocatechols and dihydrodiols that are produced as dead-end cometabolites by P. putida R5-3). These results indicate that the higher growth rate was more conducive to construction of a recombinant strain by this method.

All systems remained stable for 3 more weeks, showing no increase or decrease in chloride concentration or turbidity. After that time, a 50-ml sample was drawn out of the waste container which combined the overflows of all three chlorobenzene chemostats. The bacteria were pelleted and resuspended in 5 ml saline. From this cell suspension, 0.1 ml aliquots were spread-plated on mineral salts agar plates, which were subsequently incubated in a chlorobenzene saturated atmosphere. After 1 week of incubation, 50% of the plates showed single colonies (about 10 colonies per plate) which were restreaked on fresh plates containing bromothymol blue to confirm HCl production due to growth on chlorobenzene. Positive colonies were checked on LB and King's B for purity and origin P. putida fluoresces on King's B in contrast to P. alcaligenes. All isolates which grew on chlorobenzene fluoresced on King's B medium. One of these isolates was named P. putida CB1-9 and selected for closer investigation. Pseudomonas putida CB1-9 ATCC No. 53645, deposited at American Type Culture Collection, Rockville, Md., was found to have the following taxonomic and morphological characteristics. The organism is a gram negative rod that is catalase-positive, cytochrome oxidase-positive, motile polar flagella, does not reduce nitrates, grows only aerobically, produces fluorescent pigment on King's B, not King's A agar, hydrolyzes arganine, does not hydrolyze gelatin and produces neither acid nor gas from glucose.

Because strain CB1-9 was phenotypically similar to strain R5-3, as shown in Table 1, the possibility of spontaneous mutation in lieu of genetic exchange was considered.

TABLE 1

Catabolic phenotypes of P. alcaligenes C-O, P. putida R5-3, and P. putida CB1-9 as indicated by growth (+) or no growth (−) on substrates as sole carbon sources.

| Growth substrate | STRAINS | | |
| --- | --- | --- | --- |
| | C-O | R5-3 | CB1-9 |
| toluene | − | + | + |
| benzene | − | + | + |
| chlorobenzene | − | − | + |
| 1,4-dichlorobenzene | − | − | + |
| m-xylene | − | + | − |
| P-xylene | − | + | − |
| benzoate | + | + | + |
| 3-chlorobenzoate | + | − | + |
| 3-methylbenzoate | − | + | − |
| 4-methylbenzoate | − | + | − |

The experiment was repeated using two parallel setups according to the FIG. 1) In the first setup strain R5-3 was grown on toluene at a dilution rate of 0.010 hr$^{-1}$ in one of the upper chemostats, while the second upper chemostat of the first setup (benzoate) was run sterile at the same dilution rate. Conditions for the second setup were identical, except that C—O was grown in the benzoate chemostat. In the absence of strain C—O, the chlorobenzene chemostat turned first brown and then black, showing no chloride release over a period of 2 weeks.

After 1 and 2 weeks, samples from the overflow of this chemostat were plated on mineral medium and incubated in a chlorobenzene atmosphere as before. No acidification and chloride release within 2 weeks occurred in these plates, which all turned brown after 1–4 days of incubation. No growth occurred upon restreaking fresh plates.

When strain C—O was inoculated in the benzoate chemostat of the second setup, the chlorobenzene chemostat did not turn brown, and chloride was detected after 3 days. Samples of the chlorobenzene chemostat were spread-plated and incubated as before. Only those samples, taken after chloride release occurred in the chlorobenzene chemostat gave rise to acidification and chloride release on plates. Upon restreaking, single colonies developed on chlorobenzene plates within 2–3 days. These results clearly showed that genetic recombination between the strains R5-3, and C—O is required in order to create a chlorobenzene-utilizing strain. As before the recombinants showed the P. putida phenotype on King's B medium and were able to grown on 3CB.

P. putida CB1-9 acquired the catabolic capacity of each parental strain to grow on toluene/benzene (P. putida R5-3) and 3CB (P. alcaligenes C—O) in addition to the novel ability to grown on chlorobenzene and 1,4-dichlorobenzene (1,4-DCB). However, the recombinant was unable to grow on m- and p-xylenes, m- and p-methylbenzoates, and m- and p-chlorotoluenes. The phenotype of CB1-9 was stable in LB and benzoate media. During growth on chlorobenzene, no yellow intermediate was excreted. The maximum growth rate in pH controlled continuous culture (with NaOH) was 0.28 per-four, while growth in batch culture was linear because of increasing acidity caused by the production of HCl. Nevertheless, growth was directly proportional to chloride release. The yield coefficient, as determined from the average of all but the first and last sampling times, was 40 g cells (dry mass) per mole chlorobenzene, on the basis of O.D. 1.0=160 g/ml and stoichiometric release of chloride: this yield is comparable to that observed for P. alcaligenes C—O (34 g cells/mole) grown on 3CB (Shelton and Focht, 1985).

Growth of the recombinant on 1,4-DCB was much slower. It required about 8–9 days for complete acidification of agar plates until the pH indicator (bromothymol blue) turned completely yellow, in contrast to 1–2 days on chlorobenzene. In liquid culture, buffered with 50 mM HEPES, growth on 1,4-DCB (7 mmoles/l) was also slow ($t_d$=11 hrs). A stoichiometric amount of chloride was found in the culture after 4 weeks of incubation.

Both the R5-3, parental strain and the recombinant strain CB1-9 grew best in a 20–40% benzene saturated atmosphere, and yellow-colored metaring fission products were observed in both cultures.

Each of the parent strains was found to have a plasmid. Both of the plasmids, however, could not be cured. No exconjugants carrying both plasmids could be isolated from matings between strain C—O (pkFL1) and strain R5-3, (pkFL2). The function of both plasmids in relation to metabolism of aromatic hydrocarbons is not quite clear. The recombinant strain CB1-9 had only one plasmid, pkFL3, which according to restriction enzyme digests was derived from the 57 kb plasmid of the R %-3 parent strain by a 24 kb deletion and rearrangement of DNA.

The multiple chemostat system presented herein offers a very quick, reliable, and convenient procedure for constructing desirable microorganisms from parental strains with different but complimentary properties. This chemostat system differs from all others in that the two parental strains can be grown separately in order to maintain constant and equal cell densities of both. Moreover, separate selection pressures can be maintained in each chemostat by the use of different substrates. Also the advantage of our method over the single chemostat is that is would be possible to maintain two organisms with different growth rates, so that washout of the slower-growing strain would not be a problem. Furthermore, competition for a common substrate utilized by both of them (e.g., benzoate in this case) is also eliminated.

To confirm that both parent strains P. alcaligenes C—O and P. putida R5-3, are necessary in order to produce a chlorobenzene-utilizing recombinant, the following experiment was carried out. Four multiple chemostats using different inoculum combinations were conducted at a dilution rate of 0.01/hr (flow rate 0.07 ml/min). Color and turbidity was absent in the uninoculated multiple chemostat over the three-week period, demonstrating that aseptic conditions could be maintained.

When P. alcaligenes C—O was inoculated in the benzoate (BA) chemostat and the toluene (TOL) chemostat was not inoculated, the colors of contents in the BA, TOL and chlorobenzene (CB) chemostats were white (turbid), clear and white (turbid), respectively. No chloride was detected in the CB chemostat, nor were any CB-utilizers obtained. Thus, the turbidity in the CB chemostat was due to outflow of P. alcaligenes C—O cells from the BA chemostat.

When P. putida R5-3, was inoculated in the TOL chemostat and the BA chemostat was not inoculated, the color of the BA chemostat was clear, whereas the TOL chemostat was yellow and turbid. The color of the CB chemostat was initially brown, finally turning black due presumably to the chemical polymerization of the chlorocatechols and dihydrodiols that are the cometabolic products of P. putida R5-3. Again, chlorobenzene-degrading recombinants were not obtained, nor was chloride detected.

When both strains (R5-3, and C—O) were inoculated separately in their respective BA and TOL chemostats, all chemostats were turbid. The colors of the BA, TOL and CB chemostats in this case were white, yellow and yellow, respectively. The CB chemostat did not turn black, due to the absence of chlorinated catechols and dihydrodiols therein. Chloride was detected three days after starting the flow of liquid medium through the TOL and BA chemostats; subsequent acid production in the CB chemostat was also observed. Furthermore, single recombinant colonies developed within seven days when samples were streaked onto mineral agar plates incubated in a chlorobenzene-saturated air tank. These results clearly demonstrate that genetic exchange between both strains P. alcaligenes C—O and P. putida R5-3, is required for the generation of recombinants able to grow on chlorobenzene.

EXAMPLE 2

Construction of a Recombinant Strain Capable of Growing on m-dichlorobenzene (1,3-dichlorobenzene)

In accordance with the method of Example 1, a recombinant strain capable of growing on m-dichlorobenzene (1,3-dichlorobenzene) was isolated. It is well known that bacteria which utilize aromatic hydrocarbons as growth substrates fortuitously metabolize many chlorinated aromatic hydrocarbon analogs to dead-end products, which can not be utilized for growth. This phenomenon, referred to as "cometabolism," is believed to be effected by enzymes of low substrate specificity in the early stages of the catabolic pathway. In general, as is well recognized by those working in the field, hydrocarbon-utilizing bacteria (and especially, aromatic hydrocarbon-utilizing bacteria) and those which co-metabolize halogenated (and in particular, chlorinated) hydrocarbons define art-recognized classes of microorganisms. In particular, one skilled in the art would be able to isolate suitable microorganisms from the following genera: Pseudomonas, Alcaligenes, Acinetobacter, Arthrobacter, and to a lesser extent, Nocardia, Rhodococcus, Mycobacterium, Corynebacterium and Flavobacterium.

Figure 2:
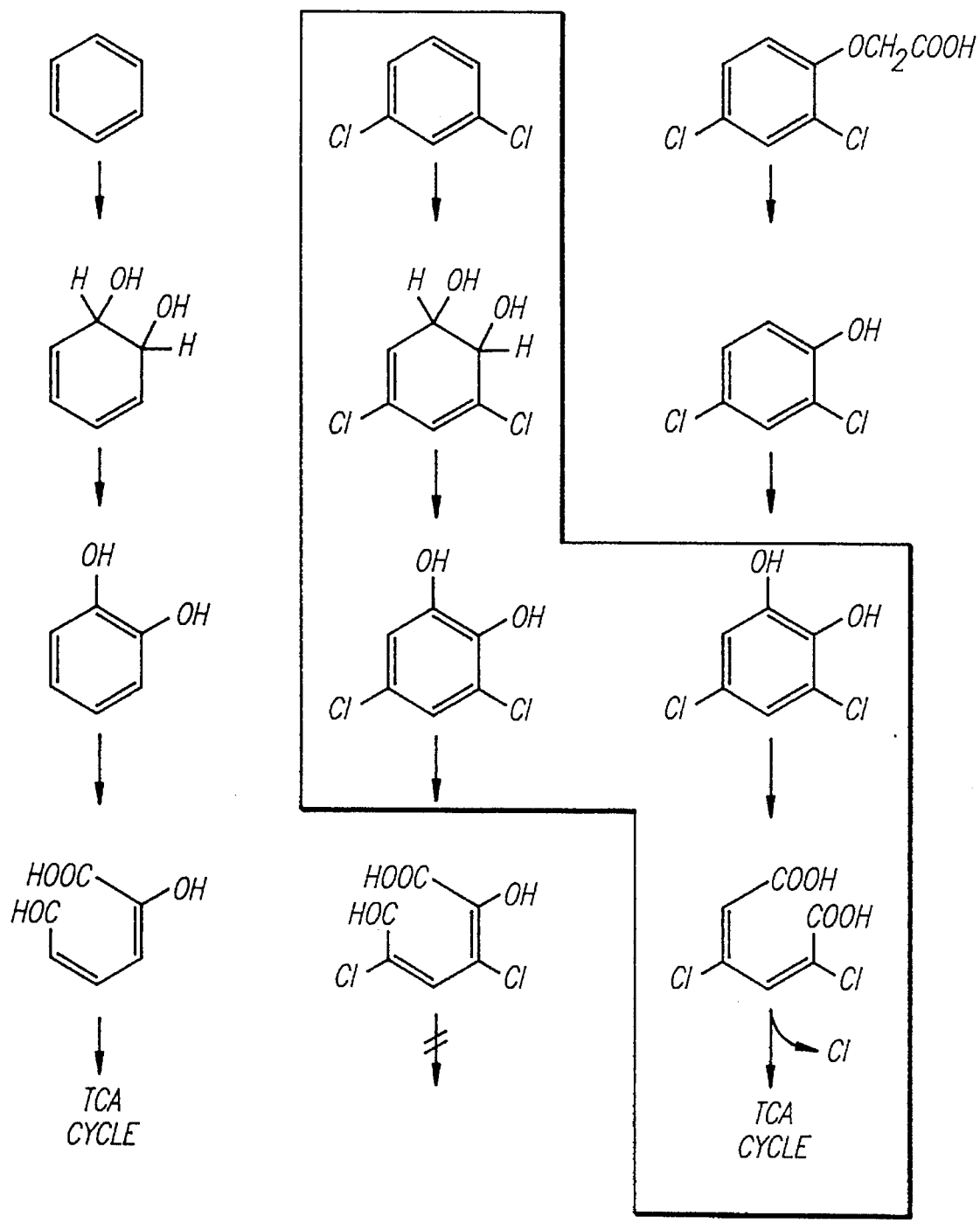
FIG. 2 illustrates degradation pathways for benzene and 1,3-dichlorobenzene in *Pseudomonas putida* R5-3 and for 2,4-dichlorophenoxyacetate in Pseudomonas sp. HF1.

All aromatic hydrocarbonoclastic bacteria without exception use a meta-fission pathway, in which the catechol intermediate is ruptured adjacent to the benzene ring; this pathway is illustrated for benzene and m-dichlorobenzene in the first and second columns, respectively, of FIG. 2. In contrast, bacteria which grow on halogenated organic acids use an ortho-fission pathway in which the catechol intermediate is ruptured between the two hydroxyl groups to give a dicarboxylic acid; this pathway is illustrated in the third column of FIG. 2. The ring fission product is eventually dehalogenated through a series of lactonization and isomerization reactions. Unfortunately, these bacteria are unable to metabolize chlorinated aromatic hydrocarbons.

As illustrated by the shading in FIG. 2, these pathways in the case of m-dichlorobenzene utilization have a common focal point, which is the 3,5-dichlorocatechol intermediate. Thus, by selecting the parent strains identified in FIG. 2, it is possible in accordance with the present invention to provide a recombinant strain which metabolizes m-dichlorobenzene according to the pathway indicated by shading in FIG. 2.

Using the same apparatus described in Example 1 with the same rationale behind the selection on chlorobenzene, a m-dichlorobenzene utilizer, Pseudomonas sp. strain CB35 was isolated from the progeny of parental matings of P. putida strain R5-3, (a chlorobenzene cometabolizer) with Pseudomonas sp. strain HF1 (a 2,4-dichlorophenoxyacetate utilizer). The procedures of Example 1 were followed, except that m-dichlorobenzene was substituted for chlorobenzene as the target compound. As noted previously, the focal point for redirection to a productive pathway was the common intermediate 3,5-dichlorocatechol. Strain R5-3, metabolized m-dichlorobenzene via the unproductive meta-fission pathway. While strain CB35 was unfortunately not maintained in viable form, both original parental strains R5-3, and HF1 have been maintained.

EXAMPLE 3

Preparation of Recombinant Capable of Metabolizing 3-Chlorobiphenyl

Figure 3:
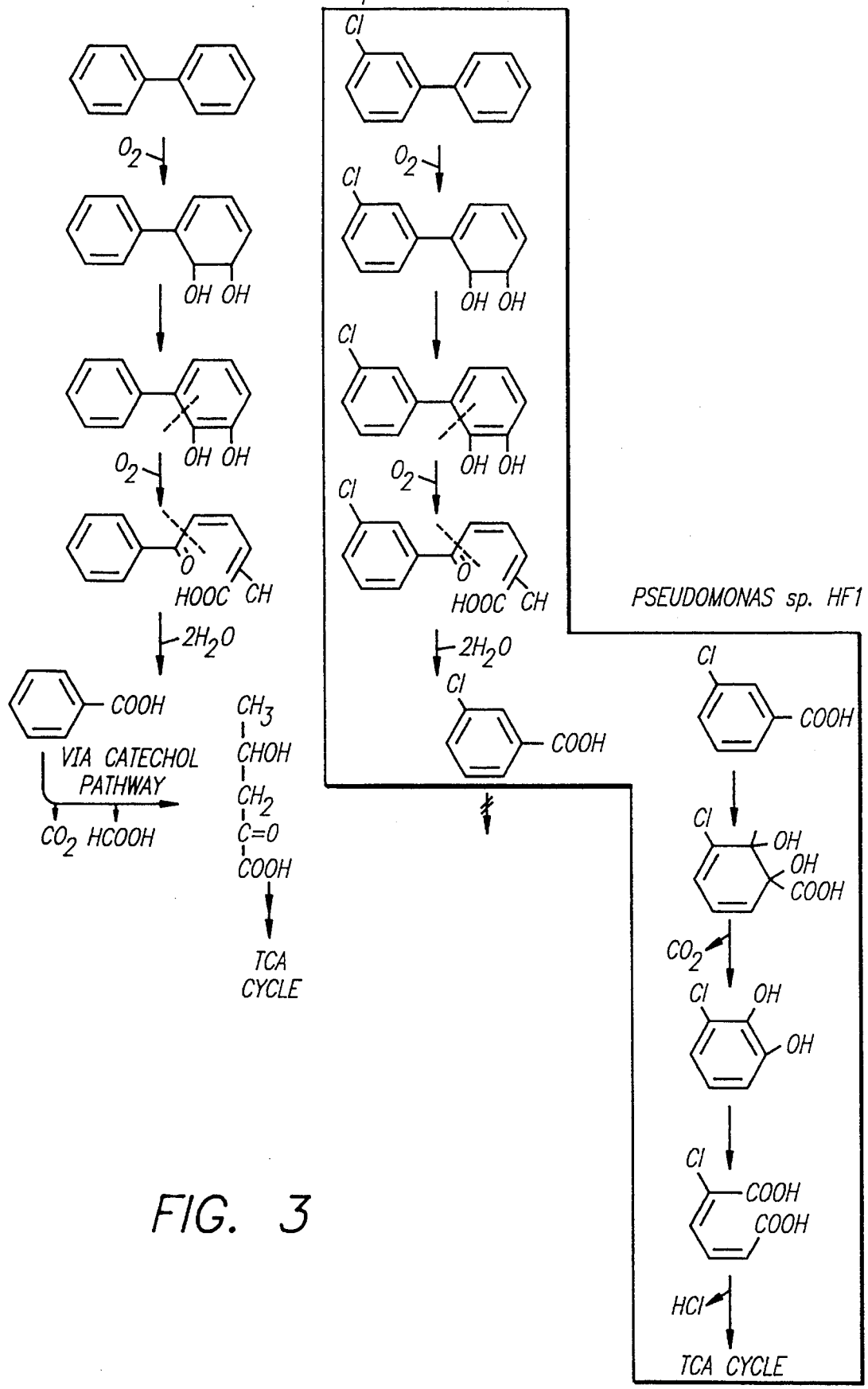
FIG. 3 illustrates degradation pathways for biphenyl and 3-chlorobiphenyl in Acinetobacter sp. P6 and for 3-chlorobenzonic acid in Pseudomonas sp. HF1.

This example describes the isolation of strain Acinetobacter sp. CB15 (which grows on 3-chlorobiphenyl and metabolizes both benzene rings with production of chloride) derived from Acinetobacter sp. P6 (a biphenyl degrader and polychlorinated biphenyl cometabolizer which degrades 3-chlorobiphenyl by a meta-fission pathway) and Pseudomonas sp. HF-1 (a 3-chlorobenzoate-utilizer employing an orthofission pathway). The relevant metabolic pathways of the parent microorganisms and the anticipated combined pathway for 3-chlorobiphenyl utilization (indicated by shading) is illustrated in FIG. 3.

Figure 4:
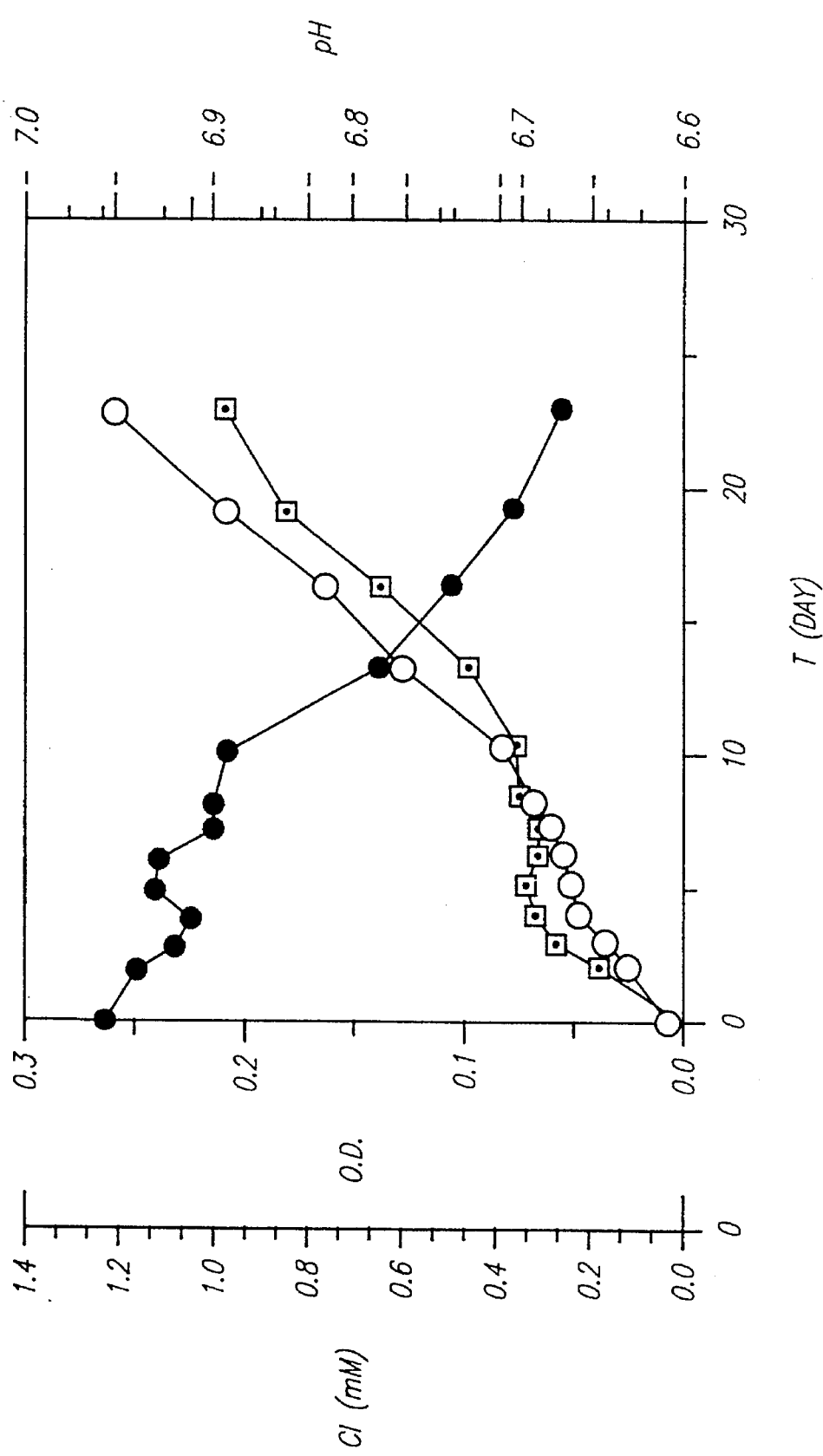
FIG. 4 reports growth of strain CB15 on 3-chlorobiphenyl as optical density, chloride production and pH change as a function of time.

As in Example 1, the parents were delivered from separate chemostats onto a column of ceramic beads. In lieu of introduction of the target compound in an admixture with air, in this instance the beads were coated with 3-chlorobiphenyl. The close proximity of the cells and the selective pressure maintained by the substrate gradient down the column amplified the genetic recombination and subsequent selection, respectively. This was evidenced by release of chloride from 3-chlorobiphenyl upon degradation of the initially-formed 3-chlorobenzoate. The recombinant is unusual in using the meta-fission pathway for catabolism of the first benzene ring, while using the ortho-fission route for catabolism of the second benzene ring. Strain CB15 grows on either 3-chlorobiphenyl or 3-chlorobenzoic acid, producing inorganic chloride. The strain does not, however, grow on 3,3'-dichlorobiphenyl. The activity to cometabolize 3,3'-dichlorobiphenyl suggests that product inhibition may prevent growth. Moreover, the possession of two potentially incompatible ring fission enzymes may also be problematical: meta-fission (of the chlorobiphenyl catechol) and ortho-fission (of the 3-chlorocatechol). Nonetheless, as illustrated in FIG. 4, growth on 3-chlorobiphenyl, while slow, reaches an optical density of 0.20 after 20 days. In FIG. 4, chloride production (●), growth as optical density, O.D. () and pH change (♦) are illustrated as a function of time.

Two metabolites produced by Acinetobacter sp. CB15 grown on 3-chlorobiphenyl were identified as 3-chlorobenzoic acid and 3-chlorocatechol. An unidentified, dead-end, black metabolite with a UV absorption maximum at 255 nm was also produced. Recombinant strain CB15 could also cometabolize 3,3'-dichlorobiphenyl with the release of inorganic chloride when it was grown on biphenyl as the growth substrate.

Recombinants as produced in accordance with the present invention are thus capable of utilizing chlorinated benzoic acids produced as dead-end products from cometabolism of biphenyl utilizers (such as Acinetobacter sp. P6) by virtue of the complementary metabolic pathway derived from the other parent, Pseudomonas sp. HF1; moreover, similar results may be obtained using other cultures representing the genera Pseudomonas, Acinetobacter and Alcaligenes isolated by enrichment culture for growth on mono- and dichlorobenzoates.

EXAMPLE 4

Isolation of Recombinant Capable of Metabolizing 2-Chlorobiphenyl

This example describes the successful isolation of a strain (designated GB-1) capable of growing on 2-chlorobiphenyl. Acinetobacter sp. P6 and *Pseudomonas aeruginosa* 2-BZZ-A (a strain isolated by 2-bromobenzoate enrichment culture from activated sewage sludge) were fed from benzoate cultures onto ceramic beads coated with PCB. In order to recognize the recombinant microbe, a sample of the lower chemostat fluid was added at several time intervals to Erlenmeyer flasks of minimal medium containing 2-chlorobiphenyl and hollow glass beads (Fisher, 4 mm). Growth was observed in the flask five days after the recombination of the strains, and a pure culture capable of growth on 2-chlorobiphenyl was obtained after restreaking on Luria agar. The resultant microbe, GB-1, is a gram negative, nonmotile rounded rod about 1 μm in diameter which does not hydrolyze gelatin and is not fluorescent or pigmented on complex media such as Luria or King A. It is positive for oxidase and catalase. These traits are all characteristic of the parent Acinetobacter sp. P6 strain, except for the positive oxidase reaction; this may have been transferred from strain 2-BZZ-A to strain P6 together with the capacity to degrade halobenzoates.

The procedure was repeated to decrease the time required to isolate the recombinant. In this instance, samples were transferred twice daily from the lower chemostat into minimal medium in flasks containing 2-chlorobiphenyl and glass beads. Total flow through the column was 39 ml/hr on the peristaltic pump. The chemostats were each of 350 ml capacity; thus, the resulting dilution rate was equivalent to 0.05 hr$^{-1}$. In flasks inoculated 36 hours or more after genetic exchange took place, a recombinant organism was again identified and designated GB-2. Its morphology and taxonomic characteristics were indistinguishable from GB-1, including the anomalous positive oxidase reaction.

The growth rates of GB-1 and GB-2 are given in Table 2. Cells (50 ml) were inoculated from a stationary phase culture grown on the substrate into a Fernbach flask of 1 liter minimal medium containing 1 g of biphenyl or 2-chlorobiphenyl. Aeration was on a gyratory shaker at 28° C. and 178 rpm. The growth rate $\mu=0.693/t_D$, where $t_D$ represents the doubling time in hours. OD is the turbidity measured at 600 nm; the "maximum" was recorded at 100 h.

TABLE 2

| Cell Type OD | Substrate | Growth rate hr$^{-1}$, μ | Lag Phase | Max |
| --- | --- | --- | --- | --- |
| GB1 | Biphenyl | 0.256 | <3.5 h | 1.1 |
| GB2 | 2-chlorobiphenyl | 0.145 | apx. 20 h | 0.248 |
| GB2 | Biphenyl | 0.435 | <3.5 h | 0.826 |
| GB2 | 2-chlorobiphenyl | 0.138 | apx 20 h | 0.284 |

When supplied with 1 g/l of substrate, both recombinants grew faster and reached a higher turbidity on biphenyl than on 2-chlorobiphenyl. The GB-2 strain exhibited a somewhat greater exponential growth rate on biphenyl than GB-1, although both organisms showed similar growth profiles on the PCB. To determine the growth range of GB2, cells were inoculated from a 2-chlorobiphenyl-grown culture into minimal medium (50 ml in a 125 ml Erlenmeyer flask) containing the test substrate at 1000 ppm, except for biphenyl derivatives (500 ppm). Determination was made after aeration on a gyratory shaker for five days. GB2 was found to grow on the following substrates: biphenyl; 2-chlorobiphenyl; 3-chlorobiphenyl; 4-chlorobiphenyl; 4-bromobiphenyl; 2-fluorobiphenyl; 4-fluorobiphenyl; 2-methylbiphenyl; 3-methylbiphenyl; 4-methylbiphenyl; 3-nitrobiphenyl; benzoic acid; 3-chlorobenzoic acid; 3-bromobenzoic acid; 4-fluorobenzoic acid; and diphenylmethane. No growth was observed on the following substrates: 2-bromobiphenyl; 3-bromobiphenyl; 3-iodobiphenyl; 2-nitrobiphenyl; 2-aminobiphenyl; 2-hydroxybiphenyl; 3-hydroxybiphenyl; 4-hydroxybiphenyl; 2-methoxybiphenyl; 2-(hydroxymethyl)-biphenyl (i.e. 2-biphenylmethanol); 2-chlorobenzoic acid; 2-bromobenzoic acid; 2-iodobenzoic acid; 2-fluorobenzoic acid; 3-iodobenzoic acid; 3-fluorobenzoic acid; 3-nitrobenzoic acid; 3-aminobenzoic acid; 3-chlorosalicylate; 3,5-dichlorobenzoic acid; phenanthrene; diphenylacetylene; ortho-terphenyl; meta-terphenyl; and para-terphenyl.

Although GB-2 is capable of growth on all three monochlorobiphenyls, chloride was only released from the meta-isomer. A white turbid culture was obtained from growth on biphenyl or 4-chlorobiphenyl, but 2-chlorobiphenyl as the sole carbon source generated a turbid yellow culture and 3-chlorobiphenyl generated a turbid russetbrown culture. No color was observed when GB-2 was grown on benzoate, 3-chlorobenzoate or 3-bromobenzoate. The ability to utilize 3-bromobenzoate labels this cell type as genuine recombinant rather than a rare mutant of P6 (an outcome unlikely to be produced so readily).

Neither recombinant can use 2-halobenzoates, a feature that allowed the isolation of the parent 2-BZZ-A strain from sewage. Only the meta-halobenzoate degradative activity (much less prominent in parent strain 2-BZZ-A than the ortho) was apparently conferred.

To evaluate the degradative activity of GB1, resting cells of the biphenyl-grown recombinant were incubated in phosphate buffer at 28° C. for 43 h with the substrate, of which 2 mg were added in 0.02 ml of DMF. The residue from rotary evaporation of the ethyl acetate acid extracts was dissolved in acetone for GC analysis by flame ionization detector on a DB-5 60 m capillary column with a starting temperature of 100° C. that was programmed at 10°/minute to a final temperature of 250° C. Metabolites were tentatively identified from the retention time of standard compounds on this temperature gradient. The following compounds were metabolized without product accumulation; 3-chlorobiphenyl; 3-methylbiphenyl; 3-hydroxybiphenyl; 4-hydroxybiphenyl; 3-chlorobenzoic acid; 3-bromobenzoic acid; 2-nitrobiphenyl; 3-nitrobiphenyl; diphenylmethane. The following were degraded with the buildup of a metabolite [in brackets]: 2-chlorobiphenyl [2-chlorobenzoic acid]; 2-bromobiphenyl [2-bromobenzoic acid]; 2-iodobiphenyl [2-iodobenzoic acid]; 4-chlorobiphenyl [4-chlorobenzoic acid; small]; 4-bromobiphenyl [4-bromobenzoic acid; large]; 2,3-dichlorobenzoic acid [2,3-dichlorobenzoic acid]; 2-methylbiphenyl [2-methylbenzoic acid]; 4-methylbiphenyl [4-methylbenzoic acid]; 2-methoxybiphenyl [2-methoxybenzoic acid]; and 2-(hydroxymethyl)biphenyl [2-(hydroxymethyl)benzoic acid (presumed)]; the following were essentially recalcitrant to GB1 oxidation: 2,2'-,3,3'-,4,4'-2,3',2,4'-dichlorobiphenyls; 2,5,2'5'-tetrachlorobiphenyl; 2,5,2',5'tetgrachlorobiphenyl; 2-hydroxybiphenyl (a slight appearance of salicylate was observed); 2-aminobiphenyl; 2-chlorobenzoic acid; 2-bromobenzoic acid; 2-iodobenzoic acid; 2-fluorobenzoic acid; 3-iodobenzoic acid; 3-fluorobenzoic acid; 4-chlorobenzoic acid; 3,5-dichlorobenzoic acid; 3,5-dibromobenzoic acid; 3-chlorosalicylate; 5-chlorosalicylate; ortho-terphenyl; and meta-terphenyl.

Growth on 2- and 4-chlorobiphenyl is a consequence of breakdown of only the unsubstituted ring; however, both rings of 3-chlorobiphenyl were broken down and chloride released. The cells grow on 3-chloro- and 3-bromobenzoate, but not 3-iodo- or 3-fluorobenzoate; this is a pattern that matches the growth profile of 2-BBZ-A. Each of the 2-halobiphenyls is converted to halobenzoate by resting cells, but only 2-chloro- and 2-fluorobiphenyls act as growth substrates. None of the PCBs bearing substituents on both rings is significantly oxidized by resting cells of GB-1. These data is consistent only with the formation of a genuine recombinant in a manner as taught herein, because of the unique total metabolism of 3-chlorobiphenyl and the ability to utilize 2-halobiphenyls as a carbon source (both of which are not possible with either parent strain).

EXAMPLE 5

Isolation of Biphenyl/Chlorobenzoate/Chlorocrotonate-Utilizing Recombinants

The continuous amalgamated culture (CAC) method of the previous examples was used for the construction of recombinant strains which can use biphenyl (BP), 3-chlorobenzoate (3CBa), and trans-3-chlorocrotonate (3CCa) as sole sources of carbon. Pseudomonas sp. CB15 and Alcaligenes sp. CC1 were used as parental strains, as these microorganisms have genes coding for the degradation of BP and 3CBa, and 3CCa respectively.

Isolation and identification of Alcaligenes sp. CC1, a chloroaliphatic-utilizer, has been described previously [Kohler-Staub, D. and H-P. E. Kohler, J. Bacteriol. 171: 1428–1434 (1989)]. Construction of recombinant strain Pseudomonas sp. CB15 is described supra. A CAC apparatus as described herein was used for the construction of recombinant bacteria. One of the upper chemostats contained Alcaligenes sp. CC1 grown on 300 ppm 3CCa in the mineral salts medium (MSM) of Example 1. The other upper chemostat contained Pseudomonas sp. CB15 grown on 300 ppm 3CBa in MSM. The column was filled with ceramic saddles which had been previously coated with 50 mg 3,3'DCBP. The lower chemostat was sampled periodically and recombinants were enriched for by sequential inoculations into broth containing 500 ppm 3CBa, 3CCa, and BP, and repeating this once. The recombinant strains, collectively designated M3G, grew on the expected products of dichlorobiphenyl transformation.

Individual colonies were isolated on plates and tested for the ability to grow on BP, 3CBa, and 3CCa. Several isolates were obtained which could grow on all three substrates. One isolate that has been characterized has been designated Pseudomonas sp. strain M3GY. This recombinant is capable of growth on 3-chlorobiphenyl.

EXAMPLE 6

Isolation of Microorganisms Capable of Metabolizing 2- and 3-Chlorobiphenyl

Microbial growth on monochlorobiphenyls is usually associated with the accumulation of the corresponding chlorobenzoate. This occurs because the organisms, although capable of growth on benzoate, are unable to metabolize the chlorinated analog. Two exceptions to this have been reported. One report described isolation of a 2- and 4-chlorobiphenyl-degrading Pseudomonas [Parsons, J. R. et al., Appl. Microbiol. Biotechnol. 29: 82–84 (1988)]. This organism metabolized certain mono- and dichlorobenzoate isomers and accumulated the corresponding chlorocatechols or chlorinated ring fission compounds. Growth on chlorobenzoates was not observed. A second report described the isolation of Alcaligenes and Acinetobacter strains from sediment which mineralized 4-chlorobiphenyl by growing on 4-chlorobenzoate [Shields, M. S. et al., J. Bacteriol. 163: 882–889 (1985)]. This latter report represents the only documented occurrence of chlorobiphenyl mineralization by pure cultures.

Chlorobiphenyl degrading organisms are clearly limited in the degradation of chlorobenzoates. Chlorobenzoates, however, are not inherently refractile. There are many reports regarding the isolation of organisms which utilize monochlorobenzoates and a few reports on 3,5- and 2,4-dichlorobenzoate. None of these chlorobenzoate-degraders, however, appears to metabolize biphenyl or chlorobiphenyls. Thus the metabolic capacity for chlorobiphenyl mineralization clearly exists; it is, however, separated in nature between two microbial populations.

Inasmuch as the potential for natural genetic exchange exists, consolidation of these activities into single organisms is conceivable. The bph genes coding for biphenyl degradation and PCB cometabolism have been postulated to be transposon-associated and thus potentially mobile [Furukawa, K. et al., J. Bacteriol. 171:5467–5472 (1989)]. The clc genes coding for chlorocatechol degradation by the modified ortho pathway are coded by a transmissible plasmid [Chaterjee, D. K. et al., J. Bacteriol. 146: 639–646 (1981); Don, R. H. et al., J. Bacteriol. 145: 681–686 (1981); Reineke, W. et al., FEMS Microbiol. Lett. 14: 291–294 (1982)]. Further, the broad-spectrum benzoate-dioxygenase carried by the TOL plasmid is transposon-associated [Tsuda, M. et al., Mol. Gen. Genet. 210: 270–276 (1987)]. It can be readily visualized how a chlorobenzoate-degrader could acquire PCB-metabolizing capability (or vice versa) giving rise to a chlorobiphenyl-mineralizing organism.

The question arises, then, as to whether genetic/physiological barriers prevent the coexistence of chlorobiphenyl and chlorobenzoate degrading activity. Possible limitations include: (1) exchange of chlorobenzoate and/or biphenyl genes in the environment at a frequency so low as to prevent detection of the new phenotype; (2) plasmid incompatibilities may prevent the establishment of new genes in the cells; or (3) selection against chlorobiphenyl-mineralizers because of enzyme incompatibilities.

The last point is supported from studies on ortho- and meta-substituted chlorocatechols. Meta- and ortho-substituted chlorobenzoates are degraded by ortho-cleavage of the corresponding mono- or dichlorocatechols. Meta-cleavage of these chlorocatechols results in unproductive or suicidal intermediates. Thus, the meta-cleavage activity associated with biphenyl/chlorobiphenyl degradation may interfere with the productive ortho-cleavage of metabolites from the chlorobenzoate pathway.

As an alternative to direct isolation, chlorobiphenyl mineralizing organisms may be obtained by pathway construction experiments. Mating experiments have been successful in constructing pathways for the degradation of chlorobenzoates, chlorophenols, and chlorobenzenes. Chlorobiphenyl mineralizing organisms have also been reported [Furukawa, K. and A. M. Chakrabarty, Appl. Environ. Microbiol. 44:619–626 (1982)]; however, it was unclear from the data presented whether chlorobiphenyl mineralization was not actually due to a coculture effect.

The strains utilized in the chemostat experiments along with relevant phenotypes are summarized in Tables 3 and 4. Phenotypes are scored as to growth/chloride release. Abbreviations: 2-, 3-CBP=2-, 3-chlorobiphenyl, respectively; 2-, 3-CBa=2-, 3-chlorobenzoate, respectively; 2,5-DCBP=2,5-dichlorobiphenyl; 2,5-DCBa=2,5-dichlorobenzoate.

TABLE 3

Phenotypes of strains used to construct Pseudomonas sp. strain UCR1

| Strain | Substrate | | | |
|---|---|---|---|---|
| | 2-CBP | 3-CBP | 2-CBa | 3-CBa |
| Ps. sp. PBP | +/− | +/− | −/− | −/− |
| Ps. aeruginosa JB2 | −/− | −/− | +/+ | +/+ |
| Ps. sp. UCR1 | +/− | +/+ | −/− | +/+ |

TABLE 4

Phenotypes of strains used to construct Pseudomonas sp. strain UCR 2

| Strain | Substrate | | | | | |
|---|---|---|---|---|---|---|
| | 2-CBP | 3-CBP | 2,5-DCBP | 2-CBa | 3-CBa | 2,5-DCBa |
| Arthrobacter sp. B1Barc | +/− | +/− | −/− | −/− | −/− | −/− |
| Ps. Aeruginosa JB2 | −/− | −/− | −/− | +/+ | +/+ | +/+ |
| Ps sp. UCR2 | +/+ | +/− | +/+ | +/+ | −/− | +/+ |

Organisms were routinely cultured in the mineral salts medium previously described, to which substrates were added to yield a final concentration of 500 μg mL$^{-1}$ (except 3-chlorobiphenyl, which was 250 μg mL$^{-1}$). Bromthymol blue (50 μg mL$^{-1}$) was included in solid mineral salts medium (MSM) as an indicator of medium acidification. Cultures were periodically grown on complex media, Luria-Bertani medium (LB) or Kings medium B(KB) to verify purity or to assay antibiotic resistance. The composition of KB has been described [King, E. O. et al., J. Lab. Clin. Med. 44: 301–307 (1954)]; LB contained (per liter) 10 g tryptone, 5 g yeast extract, and 9.5 g NaCl. Aeration for liquid cultures was provided by shaking flasks on a platform shaker at 180 RPM.

The trichemostat mating system was utilized in these experiments. Peristaltic pumps were used to replenish the chemostats with fresh media and operated at a dilution rate of 0.01 hr$^{-1}$. The chemostat housing strain JB2 was supplied with benzoate (500 μg mL$^{-1}$) in MSM. A solution of MSM alone was pumped to chemostats containing either strain P6 or strain PBP. Biphenyl was supplied as the growth substrate for these strains and was introduced into the chemostat in the vapor phase. All materials used in the construction of the trichemostat apparatus were autoclaved just prior to use.

Two separate mating experiments were conducted. In both experiments, P. aeruginosa strain JB2 was used as the chlorobenzoate-degrading parent, because it was found to grow on a wide spectrum of mono-, di-, and trihalogenated chlorobenzoates. The first mating experiment utilized Arthrobacter sp. strain B1Barc as the PCB cometabolizing parent. Strain B1Barc was isolated as a variant of Arthrobacter sp. strain B1B [Kohler, H. -P. et al., Appl. Environ. Microbiol. 54: 1940–1945 (1988)], based on colony morphology. Strain B1Barc was subsequently discovered to utilize 2-chlorobiphenyl as a carbon source, whereas the parent organism strain B1B could not. The center column was subjected to a continuous stream of chlorobenzene vapor. Samples from the collecting vessel were plated onto MSM and placed in a desiccator saturated with chlorobenzene vapors. Colonies growing on chlorobenzene were then inoculated into flasks to test for ability to grow on biphenyl and 2-chlorobiphenyl. The culture was then purified by successive streaking onto solid MSM with 2-chlorobiphenyl and then 2-chlorobenzoate.

In the second experiment, Pseudomonas sp. strain PBP was utilized as the PCB-cometabolizing parent. The center column in these experiments had been amalgamated with 2-chlorobiphenyl. This was accomplished by evaporating a solution of hexane containing 50 mg of 2-chlorobiphenyl over the sterilized ceramic beads in a laminar flow hood. Samples were withdrawn from the collecting vessel after overnight operation of the trichemostat and inoculated into MSM containing either 2-chlorobiphenyl or 3-chlorobiphenyl as a carbon source. A pair of subcultures were made on each of these substrates. The culture was finally purified by streaking on MSM with 2- or 3-chlorobiphenyl as the carbon source.

Aqueous samples were monitored for the appearance of chlorobenzoates from the degradation of chlorobiphenyls. A System Gold (Beckman Instruments Inc., San Ramon, Calif.) model 126 dual pump system was operated at a flow of 1 mL min$^{-1}$. Separation was achieved on a Versapak C-18 reverse phase column (Alltech Associates Inc., Deerfield, Ill.). An isocratic solvent system of 90% acetonitrile and 10% acetic acid (40 mM) was utilized. A model 167 UV detector (Beckman Instruments Inc., San Ramon, Calif.) was utilized to detect chlorobenzoates by measuring the absorbance at 230 nm.

Cells were prepared for oxygen uptake experiments as described above for aerobic resting cells. Measurements were made with an oxygen electrode (Yellow Springs Instrument Co., Yellow Springs, Ohio) in a 2 mL cell at 30° C. All substrates were added from 10 mg mL$^{-1}$. All rates were corrected for endogenous uptake. No oxygen consumption was observed in response to the addition of methanol alone.

Inorganic chloride was determined turbidimetrically by addition of 10 μL 0.1M AgNO$_3$ to 1 mL of acidified (5 μL H$_3$PO$_4$) sample followed by measurement at 525 nm on Uvikon model 860 UV/VIS spectrophotometer (Kontron Instruments, Zurich, Switzerland). Sample protein content was determined by using the biuret method with bovine serum albumin (Sigma Chemical, St. Louis, Mo.) as a standard [Layne, E., Methods Enzymol. 3: 447–454 (1957)].

2- and 3-chlorobiphenyl were purchased from Lancaster Synthesis Ltd. (Eastgate, Whiteland, Morecambe, England). All other PCBs were purchased from Foxboro Analabs Inc. (North Haven, Conn.). Mono- and dichlorocatechols were obtained from Helix Biotech Corporation (Richmond, BC) except 3-chlorocatechol which was supplied courtesy of F. K. Higson (U.C. Riverside). Both Kanamycin sulfate and Mitomycin C were purchased from Sigma Chemical Co. (St. Louis, Mo.). All other chemicals were obtained from Aldrich Chemical Company, Inc. (Milwaukee, Wis.).

Isolation of Pseudomonas sp. strain UCR1 was accomplished by repeated subculturing of the lower chemostat samples in liquid MSM with either 2- or 3-chlorobiphenyl as a sole carbon source. Chloride release was consistently detected in these subcultures. The liquid cultures were streaked onto solid MSM with either 2- or 3-chlorobiphenyl, and acidification due to chloride release was observed. Single colonies from these plates were inoculated into liquid MSM with either 2- or 3-chlorobiphenyl. While growth occurred on both 2- and 3-chlorobiphenyl, chloride release was detected only in cultures with 3-chlorobiphenyl.

Strain UCR1 was subsequently purified by streaking cultures onto MSM with 3-chlorobenzoate followed by inoculating single colonies into liquid MSM with 3-chlorobiphenyl. No growth on solid MSM with 2-chlorobenzoate was observed from 3-chlorobiphenyl mineralizing cultures.

The purified culture of strain UCR1 was a short, gram negative motile rod, catalase and oxidase positive, nonfluorescent on KB, and kanamycin resistant (50 μg mL$^{-1}$ in LB). This organism was thus phenotypically similar to the parental strain PBP and designated Pseudomonas sp.

Pseudomonas sp. strain UCR2 was isolated by repeated subcultures of the chemostat sample in liquid MSM with 2-chlorobiphenyl as the sole carbon source. Prior to purification, the culture was comprised of two to three colony types, as determined by growth on LB and KB; the predominant fluorescent pseudomonad was similar to strain JB2. Strain UCR2 was purified when isolated colonies were obtained on MSM with 2-chlorobenzoate. Growth on 2-chlorobenzoate in solid media was very slow, requiring about 3 weeks for the appearance of isolated colonies. When these colonies were inoculated into MSM liquid with 2-chlorobiphenyl, growth and chloride release were detected. The purified organism was a gram negative motile rod, catalase and oxidase positive, resistant to kanamycin (50 μg mL$^{-1}$ in LB) and nonfluorescent on KB. The organism was thus designated Pseudomonas sp.

The phenotype of strain UCR2, however, was sufficiently different from that of either parent to make a clear assessment of its lineage difficult. Most striking among these differences were the colony morphology, color on LB medium, and fluorescent pigment production on KB. Strain JB2 produced creamy, irregular colonies on LB and was distinctly fluorescent on KB. Strain B1Barc produced small, dry, circular, pink colonies on LB and was nonfluorescent on KB. Strain UCR2 produced large, creamy, diffuse colonies on LB but was nonfluorescent on KB.

The possibility that the phenotype of strain UCR1 could be attributed to spontaneous mutation alone in the parental strain PBP was considered. Biphenyl-grown cultures of strain PBP were plated on media containing 3-chlorobenzoate, 3-chlorobenzoate+kanamycin (50 μg mL$^{-1}$), or biphenyl+kanamycin (50 μg mL$^{-1}$). Growth was not observed on any of these media. Viable cell counts were made of the biphenyl-grown strain PBP culture tested. Based on these population determinations and the above observations, the frequency of spontaneous mutation to either 3-chlorobenzoate utilization or kanamycin resistance was thus determined to be less than $1.85 \times 10^{-9}$.

Strain UCR1 grew on 3-chlorobenzoate but was unable to utilize 2-chlorobenzoate or any dichlorobenzoates. Utilization of 3-chlorobenzoate enabled strain UCR1 to mineralize 3-chlorobiphenyl. The accumulation of insoluble black material was observed when strain UCR1 grew on 3-chlorobiphenyl but not 3-chlorobenzoate. These insoluble black materials have been noted previously from the degradation of 3-chlorobenzoate and most likely represented polymers of 3-chlorocatechol.

Strain UCR2 grew on 2-chloro and 2,5-dichlorobenzoate and on 2-chloro-, 3-chloro- and 2,5-dichlorobiphenyl; however, it did not dehalogenate 3-chlorobiphenyl. Unlike strain UCR1, strain UCR2 did not accumulate black material during growth on any chlorobenzoate or chlorobiphenyl. Dichlorobiphenyls substituted on both rings were not utilized by strain UCR2. These results are reported in Table 5 for growing cell incubations performed over an eight-week period with dichlorobiphenyls added at an initial concentration of 2.3 mM (ND=not determined; NA=not applicable).

The stability of the constructed phenotypes varied. 3-Chlorobiphenyl mineralization was not lost from strain UCR1 by subculture under nonselective conditions (i.e. growth on biphenyl). Strain UCR2, however, spontaneously lost 2-chlorobiphenyl-mineralization capability when cultured in the absence of 2-chlorobenzoate. When biphenyl-grown colonies of strain UCR2 were inoculated into liquid medium containing 2-chlorobiphenyl, growth occurred without chloride release. Analysis of culture fluid by HPLC revealed the accumulation of near stoichiometric amounts of 2-chlorobenzoate. This instability was not observed with 2-chlorobenzoate-grown cultures of strain UCR2.

TABLE 5

Utilization of Dichlorobiphenyls as Growth Substrates by Pseudomonas sp. strain UCR2

| Dichlorobiphenyl Isomer | O.D. | Chloride Release (mM) | (%) |
|---|---|---|---|
| 2,2'- | 0.003 | .03 | 0.7 |
| 2,3'- | 0.002 | ND | NA |
| 2,5- | 0.209 | 2.2 | 48.9 |

Oxygenase activities were compared between the parental strain PBP and strain UCR1 to identify the enzymatic activity gained by the latter organism. The results are reported in Table 6. The parental strain PBP was unable to metabolize any of the chlorobenzoates tested. Strain UCR1 readily oxidized 3-chlorobenzoate, but had no activity on any of the other chlorobenzoates. While both organisms had activity on 4-chlorocatechol, only strain UCR1 metabolized 3-chlorocatechol. The chlorobiphenyl-mineralizing phenotype of strain UCR1, then, could be attributed to the acquisition of 3-chlorobenzoate and 3-chlorocatechol oxidizing capabilities.

The induction of two sets of benzoate and catechol enzymes was indicated from oxygen uptake data of strain UCR1. 3-Chlorobiphenyl grown cells of strain UCR1 had much higher rates of benzoate and catechol oxidation than did 3-chlorobenzoate-grown cells. However, the rates of chlorocatechol and chlorobenzoate oxidation were greater in the 3-chlorobenzoate-grown cells. The additional enzymatic capacity induced by growth on 3-chlorobiphenyl, therefore, was not active in the metabolism of chlorinated substrates.

Induction of biphenyl/chlorobiphenyl degradation was also apparent from oxygen uptake data of strain UCR1 and the parental strain PBP. Whereas high rates of biphenyl and chlorobiphenyl oxidation were observed in biphenyl-grown cells of PBP and 3-chlorobiphenyl-grown cells of strain UCR1, only low rates were measured in 3-chlorobenzoate-grown cells of strain UCR1. Furthermore, biphenyl and chlorobiphenyl oxidation rates were much greater in 3-chlorobiphenyl-grown cells of strain UCR1, relative to the biphenyl-grown parental strain PBP.

TABLE 6

Whole Cell Oxygen Consumption of Strain UCR1 and Strain PBP

| | nmol oxygen/min. mg. protein Strain | | |
|---|---|---|---|
| Substrate | UCR1 (3CBa) | UCR1 (3CBP) | PBP (BP) |
| biphenyl | 20 | 584 | 144 |
| 2-chloro- | 23 | 316 | 82 |
| 3-chloro- | 35 | 645 | 164 |
| -benzoate | 182 | 304 | 61 |
| 2-chloro- | 0 | 0 | 0 |
| 3-chloro- | 76 | 48 | 0 |
| -catechol | 384 | 511 | 90 |
| 3-chloro- | 172 | 49 | 0 |
| 4-chloro- | 192 | 133 | 40 |

The benzoate/chlorobenzoate induction patterns in strain UCR2 differed from strain UCR1. Chlorobenzoate oxidation rates with strain UCR2 were relatively high and very similar in both 2-chlorobiphenyl- and 2-chlorobenzoate-grown cells, as shown in Table 7. Benzoate oxidation rates, however, were comparatively low and, in contrast to chlorobiphenyl-grown strain UCR1, were not enhanced in 2-chlorobiphenyl-grown cells.

Strain UCR2 was similar to strain UCR1, in that high levels of catechol activity were induced in chlorobiphenyl-grown cells. In contrast to chlorobiphenyl-grown strain UCR1, however, chlorobiphenyl-grown cells of strain UCR2 exhibited higher rates of chlorocatechol oxidation relative to 2-chlorobenzoate-grown cells. Chlorobiphenyl-grown cells of strain UCR2 further differed from strain UCR1 in that accumulation of yellow products was observed during the metabolism of catechol and 4-chlorocatechol. These accumulations were not observed with 2-chlorobenzoate-grown cells of strain UCR2.

TABLE 7

Oxygen Uptake by Whole Cells of Strain UCR2

| | (nmol oxygen consumed/min mg protein) Growth Substrate | |
|---|---|---|
| Test Substrate | 2-chlorobiphenyl | 2-chlorobenzoate |
| biphenyl | 206 | 7 |
| 2-chloro- | 208 | 7 |
| 3-chloro- | 239 | ND |
| 4-chloro- | 0 | ND |
| -benzoate | 5 | 7 |
| 2-chloro- | 36 | 36 |
| 3-chloro- | 7 | 4 |
| 2,3-dichloro- | 7 | 4 |
| 2,5-dichloro- | 34 | 40 |
| -catechol | 359* | 57 |
| 3-chloro | 144 | 46 |
| 4-chloro | 48* | 36 |

*Accumulation of yellow ring fission product.

In this experiment, chlorobenzene was utilized as the target substrate in the construction of strain UCR2. The apparent result was the transfer of 2-chloro- and 2,5-dichlorobenzoate degrading activity. In contrast, using 2-chlorobiphenyl as the target substrate for the construction of strain UCR1 resulted in the transfer of 3-chlorobenzoate-degrading activity. The above results indicate the target substrate in the column may exert an indirect or minimal effect on the gene transfer process. Gene transfer is more likely dependent on the nature of the organisms utilized, (i.e. the ability to serve as donors or recipients), and the nature of the genes of interest (i.e., the association with mobilizable elements).

Although the mechanisms have not been elucidated, the evidence indicated that the transconjugants were constructed by activity donated to the PCB-cometabolizing parent from the chlorobenzoate degrader. This was most clearly indicated by the comparison of Pseudomonas sp. strain UCR1 with the parental organisms, Pseudomonas aeruginosa strain JB2 and Pseudomonas sp. strain PBP. Strain UCR1 was clearly a Pseudomonas sp. and thus derived from the parental strain PBP. Comparisons of strains PBP and UCR1 thus indicated the phenotype of strain UCR1 required the acquisition of both 3-chlorobenzoate and 3-chlorocatechol oxidizing activity by the PCB cometabolizing parent Pseudomonas sp. strain PBP.

Unlike strain UCR1, the lineage of strain UCR2 was not unequivocally established. Discussion as to the events leading to the construction of this organism is therefore speculative. However, there is only a single report on the isolation of chlorobiphenyl-mineralizing organisms (Shields et al., supra), and the isolation of dichlorobiphenyl-mineralizing organisms has never been described. It is highly unlikely, then, that strain UCR2 was a preexisting phenotype fortuitously isolated as a contaminant from the chemostat culture.

The coordination of biphenyl and chlorobenzoate activities in strains UCR1 and UCR2 had a number of differences as well as similarities. In both organisms, chlorobenzoates did not serve as inducers of the biphenyl/chlorobiphenyl-degradation genes. Strain UCR1 and UCR2 were also similar in that growth on chlorobiphenyls induced high levels of catechol activity. Strain UCR1 and UCR2 differed principally in the induction of benzoate oxidation by growth on chlorobiphenyls. In the case of strain UCR1, high levels were induced after growth on 3-chlorobiphenyl while no induction occurred in strain UCR2 after growth on 2-chlorobiphenyl.

The above observations regarding catechol activity indicated that meta-cleavage activities of the biphenyl pathway are not incompatible with ortho-cleavage of chlorobenzoate degradation. Incompatibilities were avoided as the phenylcatechol dioxygenase of the biphenyl meta-pathway did not utilize 3-chlorocatechol (the primary intermediate in the degradation of 2- and 3-chlorobenzoate) as a substrate. This limitation in phenylcatechol activity was indicated by two observations. First, although dramatic increases in catechol activity were noted in chlorobiphenyl-grown cells of both strains UCR1 and UCR2, activity on chlorocatechols increased only slightly in the latter and decreased in the former. Second, the products of meta-cleavage activity were observed in strain UCR2 from catechol and 4-chlorocatechol, but not 3-chlorocatechol.

The experiments reported above were successful in consolidating chlorobenzoate and biphenyl-degrading abilities, to produce chlorobiphenyl-mineralizers. The question arises as to why similar organisms are not more commonly isolated from natural sources. As indicated above, the phenotypes are not prohibited due to enzyme incompatibilities. A potential reason, however, may be genetic instabilities. This was true with strain UCR2 which required the presence of 2-chlorobenzoate for the maintenance of the chlorobiphenyl-mineralizing phenotype. Instability of chlorobenzoate degradation was also observed in the 4-chlorobiphenyl-mineralizing organisms isolated by Shields et al., supra. Thus, chlorobiphenyl-mineralizing organisms might arise naturally from gene exchange in the environment. However, without strong selection pressure (as provided in accordance with the present invention), these phenotypes might not proliferate or persist; this would make isolation from natural sources difficult, if not impossible.

While certain specific embodiments of the invention have been disclosed as typical, the invention is, of course, not limited to these particular forms but rather is applicable to all such variations as fall within the scope of the appended claims. For example, several strains of microorganisms can be used to contribute the necessary catabolic enzymes to the recombinant strain.

What is claimed is:

1. In a process for recovery of a recombinant bacterium having a total genetic capability for carrying out a given metabolic function, said recombinant bacterium being derived from two parent bacteria between which genetic exchange can occur and which in combination contain said total genetic capability but which do not individually contain said total genetic capability, said metabolic function comprising a sequence of metabolic steps necessary for catabolism of an organic compound substrate, wherein each said metabolic step of said metabolic function is catalyzed by an enzyme encoded by a gene and said total genetic capability comprises a complete set of said genes corresponding to all enzymes necessary for catabolism of said organic compound substrate, the improvement comprising:

culturing said two parent bacteria separately in chemostats under conditions which establish individual cultures of each of said two parent bacteria at steady state growth; and mixing portions of said cultures under conditions which promote contact between said two parent bacteria and which select for said recombinant bacterium capable of carrying out said given metabolic function, wherein genetic exchange between said two parent bacteria and survival of only said recombinant bacterium having said given metabolic function is promoted.

2. The process according to claim 1 wherein said mixing is carried out in an adsorbent column.

3. The process according to claim 2 wherein said adsorbent column is a ceramic bead column.

4. The process according to claim 2 wherein effluent from said adsorbent column is introduced into a further chemostat and said recombinant bacterium is cultured in said further chemostat.

5. The process according to claim 4 wherein said recombinant bacterium is isolated from a culture thereof in said further chemostat.

6. The process according to claim 1, wherein each of said parent bacteria is of a genus independently selected from the group consisting of Pseudomonas, Alcaligenes, Acinetobacter, Arthrobacter, Nocardia, Rhodococcus, Mycobacterium, Corynebacterium and Flavobacterium.

7. The process according to claim 6, wherein said genus is Pseudomonas, Alcaligenes, Acinetobacter or Arthrobacter.

* * * * *

UNITED STATES PATENT AND TRADEMARK OFFICE
CERTIFICATE OF CORRECTION

PATENT NO. : 5,578,474

DATED : November 26, 1996

INVENTOR(S) : Dennis D. Focht and Lothar P. Kröckel

It is certified that error appears in the above-indentified patent and that said Letters Patent is hereby corrected as shown below:

| COLUMN | LINE | |
|---|---|---|
| 5 | 41 | "$MgSO_4, 7H_2O$" should be --$MgSO_4 \cdot 7H_2O$-- |
| 6 | 48 | ";" should be -- : -- |
| 6 | 55 | "Conugation" should be --Conjugation-- |
| 7 | 22 | "origin P. putida" should be --origin. *P. putida*-- |
| 7 | 59 | "FIG. 1)" should be --FIG. 1.-- |
| 8 | 19 | "grown" should be --grow-- |
| 8 | 24 | "grown" should be --grow-- |
| 8 | 31 | "per-four," should be --per hour,-- |
| 8 | 49 | "R5-3," should be --R5-3-- |
| 8 | 56 | "R5-3," should be --R5-3-- |
| 8 | 61 | "R %-3" should be --R5-3-- |

UNITED STATES PATENT AND TRADEMARK OFFICE
CERTIFICATE OF CORRECTION

PATENT NO.   : 5,578,474
DATED        : November 26, 1996
INVENTOR(S)  : Dennis D. Focht and Lothar P. Kröckel It is certified that error appears in the above-indentified patent and that said Letters Patent is hereby corrected as shown below:

| COLUMN | LINE | |
|---|---|---|
| 9  | 5  | "is that is" should be --is that it-- |
| 9  | 11 | "R5-3," should be --R5-3-- |
| 9  | 28 | "R5-3," should be --R5-3-- |
| 9  | 38 | "R5-3," should be --R5-3-- |
| 9  | 53 | "R5-3," should be --R5-3-- |
| 10 | 39 | "R5-3," should be --R5-3-- |
| 10 | 45 | "R5-3," should be --R5-3-- |
| 10 | 49 | "R5-3," should be --R5-3-- |
| 11 | 24 | "()" should be --(■)-- |
| 13 | 36 | "4,4'-2," should be --4,4'-,2,-- |
| 22 | 28 | "wherein" should be --whereby-- |

Signed and Sealed this

Eighth Day of July, 1997

Attest:

BRUCE LEHMAN

Attesting Officer    Commissioner of Patents and Trademarks